(12) United States Patent
Almeflo

(10) Patent No.: US 11,744,738 B2
(45) Date of Patent: Sep. 5, 2023

(54) HEARING PROTECTOR HAVING A UNIDIRECTIONAL SOUND INLET

(71) Applicant: 3M INNOVATIVE PROPERTIES COMPANY, St. Paul, MN (US)

(72) Inventor: Per Ove Almeflo, Järfälla (SE)

(73) Assignee: 3M Innovative Properties Company, St. Paul, MN (US)

(*) Notice: Subject to any disclaimer, the term of this patent is extended or adjusted under 35 U.S.C. 154(b) by 284 days.

(21) Appl. No.: 15/733,186

(22) PCT Filed: Dec. 6, 2018

(86) PCT No.: PCT/IB2018/059737
§ 371 (c)(1),
(2) Date: Jun. 5, 2020

(87) PCT Pub. No.: WO2019/111214
PCT Pub. Date: Jun. 13, 2019

(65) Prior Publication Data
US 2020/0383834 A1    Dec. 10, 2020

(30) Foreign Application Priority Data
Dec. 8, 2017 (EP) ..................... 17206065

(51) Int. Cl.
*A61F 11/14* (2006.01)
*H04R 1/10* (2006.01)

(52) U.S. Cl.
CPC ............ *A61F 11/14* (2013.01); *H04R 1/1008* (2013.01)

(58) Field of Classification Search
CPC ........ A61F 11/14; A61F 11/08; A61F 11/145; A61F 11/12; A61F 11/085; A61F 11/06;
(Continued)

(56) References Cited

U.S. PATENT DOCUMENTS

| 7,103,188 | B1* | 9/2006 | Jones | ............... G10K 11/17833 381/71.13 |
| 8,651,229 | B2* | 2/2014 | Franzen | .................. A61F 11/14 381/372 |

(Continued)

FOREIGN PATENT DOCUMENTS

| EP | 2671547 | 12/2013 |
| FR | 2579455 | 10/1986 |

(Continued)

OTHER PUBLICATIONS

International Search report for PCT International Application No. PCT/IB2018/059737 dated Mar. 15, 2019, 6 pages.

*Primary Examiner* — Lun-See Lao
(74) *Attorney, Agent, or Firm* — Katherine M. Scholz

(57) ABSTRACT

There is provided a hearing protector that has an earmuff (2) formed by a cup-shaped shell and a cushion. The hearing protector has a sound inlet (5) formed of at least one acoustic membrane that replaces a portion of the shell or by a hole into the cushion. The sound inlet locally reduces the sound barrier of the hearing protector predominantly with respect to sound originating from an anterior direction (11) that is defined in accordance to on the anatomic directions of a wearer when the hearing protector is worn. The present disclosure helps enabling directional hearing with a hearing protector.

14 Claims, 9 Drawing Sheets

(58) Field of Classification Search
CPC .................. A61F 9/029; A61F 2230/00; A61F 2230/0065; A61F 11/10; A61F 2210/0076; A61F 2250/0004; A61F 2250/0009; A61F 2250/0012; A61F 2250/0075; A61F 2250/008; A61F 9/02; A61F 9/06; A61F 9/065; A61F 9/067; A61F 9/068; A61F 2240/008; H04R 1/1083; H04R 1/1008; H04R 1/1016; H04R 25/554; H04R 25/405; H04R 25/604; H04R 25/652; H04R 25/658; H04R 5/033; H04R 2420/07; H04R 2201/107; H04R 1/1041; H04R 1/12; H04R 1/1075; H04R 2460/15; H04R 5/0335; H04R 1/2842; H04R 1/2857; H04R 1/288; H04R 2430/20; H04R 25/407; H04R 25/552; H04R 3/005; H04R 1/1066; H04R 2460/13; H04R 1/10; H04R 1/08; H04R 1/083; H04R 1/1058; H04R 17/005; H04R 2225/43; H04R 2460/17; H04R 25/43; H04R 25/656; H04R 29/00; H04R 1/04; H04R 1/46; H04R 2430/03; H04R 2460/01; H04R 25/356; H04R 25/453; H04R 25/558; H04R 5/00; H04S 2400/15; H04S 2420/01; G10L 21/0208; G10L 25/18; H04M 1/19; H04M 1/05; H04M 1/6041

USPC ..................................................... 381/74, 312

See application file for complete search history.

(56) References Cited

U.S. PATENT DOCUMENTS

| | | |
|---|---|---|
| 2004/0184630 A1 | 9/2004 | Ach-Kowalewski |
| 2010/0128885 A1 | 5/2010 | Roos |
| 2011/0064239 A1 | 3/2011 | Sjöman |
| 2012/0076334 A1* | 3/2012 | Anderson ............ H04R 25/505 381/317 |
| 2013/0343559 A1* | 12/2013 | Ohlander ............ H04R 1/2811 381/72 |

FOREIGN PATENT DOCUMENTS

| | | | | |
|---|---|---|---|---|
| GB | 1243728 A | | 8/1971 | |
| GB | 2075849 | | 11/1981 | |
| WO | WO 91/07152 | * | 5/1991 | ............ A61F 11/14 |
| WO | WO 1991-007153 | | 5/1991 | |
| WO | WO 1994-009734 | | 5/1994 | |
| WO | WO 2019/104172 | | 5/2019 | |

* cited by examiner

HEARING PROTECTOR HAVING A UNIDIRECTIONAL SOUND INLET

CROSS REFERENCE TO RELATED APPLICATIONS

This application is a national stage filing under 35 U.S.C. 371 of PCT/IB2018/059737, filed Dec. 6, 2018, which claims the benefit of EP Application No. 17206065.9, filed Dec. 8, 2017, the disclosure of which is incorporated by reference in its/their entirety herein.

FIELD

The present disclosure relates to a hearing protector that has a sound inlet for locally and unidirectionally weakening the attenuation of the hearing protector so as to enable a person directional hearing while wearing the hearing protector.

BACKGROUND

Hearing protectors are typically used in noisy environments for protecting a wearer's hearing from noise at potentially harmful noise levels. Typically, hearing protectors have two earmuffs or caps which cover the ears of the wearer and which are connected to one another by a headband. Each cup further typically is formed by a rigid shell that is furnished with a noise dampening material, for example a foamed material.

There is a general desire to make hearing protectors user-friendly, in particular to encourage persons that are in noisy environments for longer times to actually wear the protectors. While noise dampening is an essential purpose of a hearing protector, there is often a need for the wearer to hear certain sounds from the environment, like acoustic signals, instructions, or conversations. Further, there is often a desire for the wearer to use the hearing protector as headset for radio or telephone applications.

There are active hearing protectors on the market which have passive noise dampening properties and additionally are configured to transmit sounds from the environment into the ear cup via active electronics connected to a microphone outside the ear cup and a loud speaker inside the ear cup. Such hearing protectors are typically set up so that the active sound transmission is restricted to a pre-determined level with respect to the human hearing. Sound levels from the environment that exceed that pre-determined level are dampened due to the passive dampening properties of the hearing protector.

Further, passive hearing protectors can be typically selected from different levels of passive attenuation to allow a wearer to hear sounds above a certain level while generally protecting the wearer's ear from harmful sound levels. There is however a desire that the wearer of a hearing protector is enabled to perceive any sound passing through the hearing protector generally at a quality at which the wearer would perceive the original sound without wearing the hearing protector, but just at a lower sound level. Many hearing protectors, however, naturally reduce the sound quality, in particular modify the sound and thereby affect particularly the capability of the wearer to perceive a direction from which the sound originates.

Therefore, there is a need for a hearing protector which facilitates directional hearing for a wearer.

SUMMARY

The present disclosure in a first aspect relates to a hearing protector having an earmuff that is provided with a direction dependent attenuation or a direction dependent sound barrier.

In particular, the present disclosure relates to a hearing protector that comprises an earmuff. The earmuff comprises a cup-shaped shell. The cup-shaped shell provides for a sound attenuation or a sound barrier. The hearing protector further comprises a sound inlet that is formed of at least one acoustic membrane that replaces a portion of the shell. Preferably the sound inlet locally reduces the sound barrier of the shell predominantly with respect to sound originating from an anterior direction. In other words, the sound inlet may provide a unidirectional weakening of the sound attenuation or sound barrier of the shell in the anterior direction. The anterior direction is defined in accordance to the anatomic directions of a wearer when the hearing protector is worn.

The present disclosure allows for an additional sound transmission through the hearing protector for sound originating from a particular direction. In other words, the present disclosure provides a hearing protector with an attenuation that is only locally and in one direction weakened. Therefore, the hearing protector facilitates so-called directional hearing when worn by a wearer. The term "directional hearing" as referred to in this specification is understood to mean a hearing that includes a perception of a direction from which the sound originates. Accordingly, a wearer wearing the hearing protector of the present disclosure can determine a direction from which a sound is originating better than with wearing a conventional hearing protector. This helps maximizing the wearing comfort. Further this helps maximizing the safety, for example in case a source of danger (for example an approaching forklift) has to be recognized while the hearing protector is worn.

The earmuff is typically formed of a front portion that faces in the anterior direction, and a rear portion facing in a posterior direction which is the direction opposite of the anterior direction. In some embodiments, the front portion and the rear portion of the earmuff are preferably monolithically formed. In some embodiments, the front and rear portion may not be distinguishable from the shape of the earmuff alone. The front portion may for example be formed by that half of an earmuff that is oriented to the anterior direction and the posterior portion may be the opposite half when the hearing protector is worn by a wearer. Preferably the sound inlet is provided predominantly within the front portion. That means that one or more sound inlets may be only provided within the front portion. In case several sound inlets are provided, most of the sound inlets are preferably provided in the front portion. Further, a sound inlet that overlaps with the front and rear portion is preferably offset more toward the front portion than toward the rear portion. The arrangement of the sound inlet predominantly in the front portion is one way of unidirectionally weakening the sound barrier of the earmuff.

In some embodiments, the membrane exhibits a resonance frequency that is within a range of 1000 Hz to 10000 Hz or 3000 Hz to 6000 Hz. In this frequency range directional hearing is to a significant extent based on a sound level difference of sound originating from different directions. It is noted that, for the purpose of the present specification, the direction from which the sound originates is determined between the anterior direction of a person's head wearing the hearing protector and the direction from which the sound originates. This means that a level difference of the same sound may occur in case a wearer of the hearing protector turns their head although the source of the sound does not move.

In some embodiments, the shell of the earmuff is formed by a shell wall that has a smallest shell wall thickness and wherein the membrane is formed by a membrane wall that has a greatest membrane thickness. The smallest shell wall thickness is greater than the greatest membrane thickness. In other words, the membrane is thinner than the thinnest portion of the shell wall. The smallest shell wall thickness is preferably within a range of 2 mm to 6 mm. A typical wall thickness of a shell wall is 4 mm. Further, the greatest membrane thickness is preferably within a range of 0.1 mm to 1 mm, in particular 0.2 mm. The membrane extends in a first and a second dimension. The smallest dimension in each of the first and second dimension is preferably between 5 mm and 20 mm, more preferably between 8 mm and 12 mm. The membrane may have a circular, elongated or arced shape. The membrane may for example have a diameter of 10 mm and a thickness of 0.2 mm.

In some embodiments, the membrane is oriented in the anterior direction or at an angle of less than 90 degrees from the anterior direction. In some embodiments, the membrane is oriented so that it can pick up sound from the anterior direction at a higher sound level than the same sound originating from the opposite direction.

In some embodiments, the membrane is made of a plastic material selected from among a thermoplastic polyurethane (TPU), acrylonitrile-butadiene-styrene terpolymer (ABS), polyvinylchloride (PVC), polypropylene (PP) and silicone.

In some embodiments, the hearing protector, in particular each earmuff, comprises two or more membranes each replacing a portion of the shell. The membranes in combination with each other together form the sound inlet.

In some embodiments, the hearing protector further comprises a cushion that is arranged at the earmuff for sealing with the wearer's head around the ear.

In some embodiments, the earmuff further comprises an attenuation insert. Such an attenuation insert may be formed of a foamed material, for example.

In a second aspect the present disclosure relates to a hearing protector that comprises an earmuff. The earmuff comprises a cup-shaped shell. The cup-shaped shell provides for a sound attenuation or a sound barrier. The hearing protector further comprises a cushion for sealing on a wearer's head. The hearing protector comprises a sound inlet formed of at least one hole, preferably a blind-hole, in the cushion. The sound inlet preferably locally reduces the sound barrier of the cushion predominantly with respect to sound originating from an anterior direction. In other words, the sound inlet may provide a unidirectional weakening of the sound attenuation or sound barrier of the shell in the anterior direction. The anterior direction is defined in accordance to the anatomic directions of a wearer when the hearing protector is worn.

The first and second aspect of the present disclosure may be used individually or in combination.

In some embodiments, the cushion is ring-shaped and forms a head facing side for contacting a wearer's head and an outer circumferential side extending between the earmuff and the head facing side. The outer circumferential side is formed of a front portion and a rear portion. The front and rear portion are located toward the anterior direction and the posterior direction, respectively, when the hearing protector is worn by a wearer. Preferably the cushion comprises at least one hole through the front portion of the outer circumferential side. The rear portion may be free of holes or may comprise less holes than the front portion. In particular a front open area provided by the hole(s) through the front portion of the outer circumferential side is preferably larger than a rear open area provided by the hole(s) through the rear portion of the outer circumferential side. In some embodiments, the holes are preferably blind holes into the cushion. Thus, the attenuation provided by the cushion is not weakened too much.

In some embodiments, the cushion comprises seven holes through the front portion of the outer circumferential side. Each of the 7 holes through the front portion of the outer circumferential side has a diameter of 4 mm. In some embodiments, the rear portion of the outer circumferential side may have no holes of a number of holes of up to 22. Thereby each of the 22 holes may have a diameter within a range of between 0.5 mm and 1 mm, for example 0.75 mm. It has been found that in some embodiments, the directional hearing effect is particularly significant at about a sound frequency of about 2 kHz. Further, the most significant directional hearing effect is achieved with 7 holes of 4 mm diameter each through the front portion of the outer circumferential side and with 6 holes of 1 mm diameter each through the rear portion of the outer circumferential side.

In some embodiments, the earmuff comprises a loudspeaker. The hearing protector may have electronic circuitry for driving the loudspeaker. Further, the hearing protector may have a microphone, and the electronic circuitry in combination with the loudspeaker and the microphone may provide a communication module. Such a communication module may enable a communication of two persons at least one of whom wearing a hearing protector of the present disclosure.

The hearing protector of any of the first and/or second aspect of the present disclosure preferably comprises two earmuffs in accordance with the embodiments of the present disclosure. The hearing protector may further comprise a headband that connects the two earmuffs. The hearing protector may further comprise two cushions arranged at the earmuffs in accordance with the embodiments of the present disclosure.

DETAILED DESCRIPTION

Figure 1:
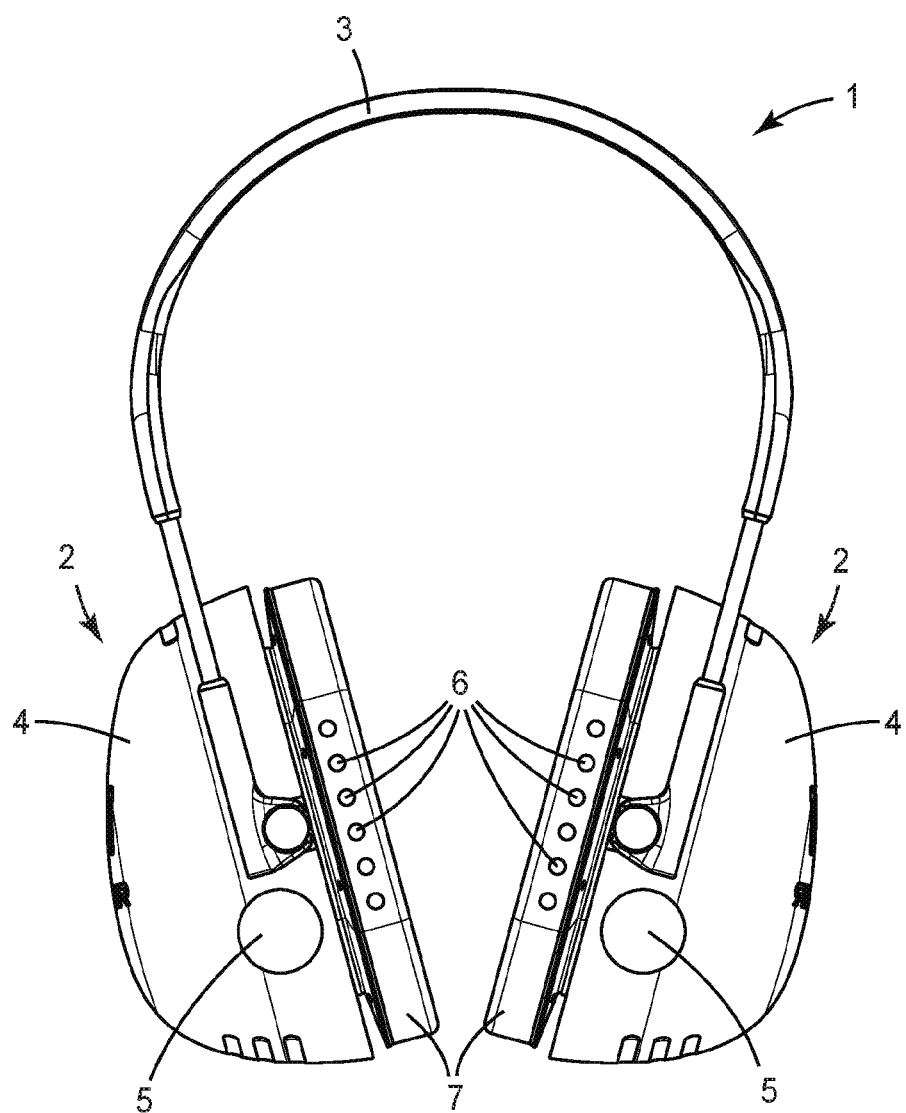
FIG. 1 is a front view of a hearing protector according to some embodiments of the present disclosure.

FIG. 1 shows a hearing protector 1 according to the present disclosure. The hearing protector 1 has two earmuffs 2 that are suspended at a headband 3. Although in the example a particular type of headband is shown, the skilled person will recognize that there are different types of headbands for hearing protectors that may be likewise used with the present disclosure.

The earmuff comprises a cup-shaped shell 4. The shell 4, when the hearing protector is worn, encloses the ear of a wearer and provides a barrier for sound that approaches the wearer's ear. A barrier for sound as referred to herein means that any sound transmitted through the shell is reduced in its sound level by the shell. The shell 4 is formed by a closed shell wall. Each earmuff 2 further has an acoustic membrane 5 that replaces a portion of the shell 4, in particular a portion of the shell wall. The acoustic membrane 5 in the example is provided by a thinned area in the overall shell wall. That thinned area has a wall thickness that is reduced with respect to the remainder of the wall that forms the shell. Although in this example the membrane 5 is monolithically formed with the remainder of the shell wall, in another example the membrane may be a separate part that closes an opening in the shell wall. The acoustic membrane 5 forms a sound inlet into the earmuff 4. The sound inlet is based, on the one hand, on a reduced sound attenuation due to the reduced wall thickness. On the other hand the acoustic membrane has a resonance frequency naturally provided by the configuration of the acoustic membrane 5. The acoustic membrane 5 can be configured or tuned toward a desired resonance frequency to permit certain sound frequencies to be transmitted through the membrane 5 at preference. Overall, the acoustic membrane provides for a preferred sound transmittance through a local area of the earmuff.

The acoustic membrane 5 in the example is oriented toward an anterior direction. In particular the membrane 5 in the example faces the anterior direction. The anterior direction is defined in accordance to on the anatomic directions of a wearer when the hearing protector is worn. In other words, the acoustic membrane 5 is oriented in the same direction as the wearer's eyes when the hearing protector is worn. Thereby the hearing protector has (in particular each of the earmuffs have) a capability to pick up sound originating from the anterior at preference.

Each of the earmuffs 2 further has a cushion 7. The cushion 7 is ring-shaped. Further, the cushion 7 is resilient. Thus, the cushion 7 can conform to the wearer's head and seal the wearer's ear from the environment. Each cushion 7 has a plurality of holes 6. The holes 6 are arranged into a surface of the cushion 6 that faces in the anterior direction. Further the holes 6 are only or predominantly arranged into the surface of the cushion 6 that faces in the anterior direction. Thereby the cushion's sound attenuation properties are weakened at an area that is oriented toward the anterior direction. Accordingly the earmuffs 4 by the holes are provided with a preferred capability to pick up sound originating from the anterior.

The cushion 7 is basically formed by a ring-shaped tube of a plastic liner that is filled with a foamed material. The holes 6 are through-holes through the liner. However, in some embodiments, the through-holes do not extend through the entire cushion. Thereby the sound attenuating properties of the cushion may be weakened but not eliminated.

It has been found that the acoustic membrane 5 in the shell 4 and the holes 6 in the cushion 7 can be configured for providing a preferred transmittance of sound of different frequency ranges. For example, the acoustic membranes have resulted in a preferred transmittance of sound in higher frequency ranges, whereas the holes have resulted in a preferred transmittance of sound in lower frequency ranges. The skilled person will however recognize that the acoustic membrane as well as the holes may be varied in configuration for tuning the sound transmittance toward desired ranges.

With the configuration of the hearing protector as described a wearer is enabled to recognize a direction from which a sound originates. This was tested as described in the following.

Figure 2:
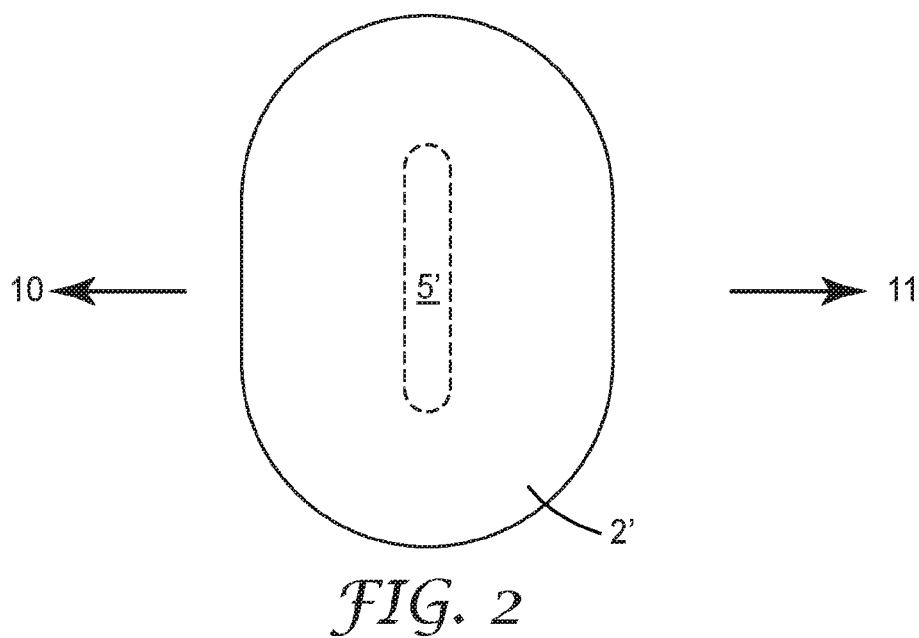
FIG. 2 is a top view on an earmuff for a hearing protector which is not in accordance with the present disclosure.

FIG. 2 shows a top view onto an earmuff 2' that is not in accordance to the present disclosure. In the example the earmuff 2' has an acoustic membrane 5' which is arranged symmetrically. This means that the attenuation provided by the earmuff 2' to sound originating from the anterior direction 10 is the same (or essentially the same) as the attenuation provided by the earmuff 2' to sound originating from the posterior direction 11.

Figure 3:
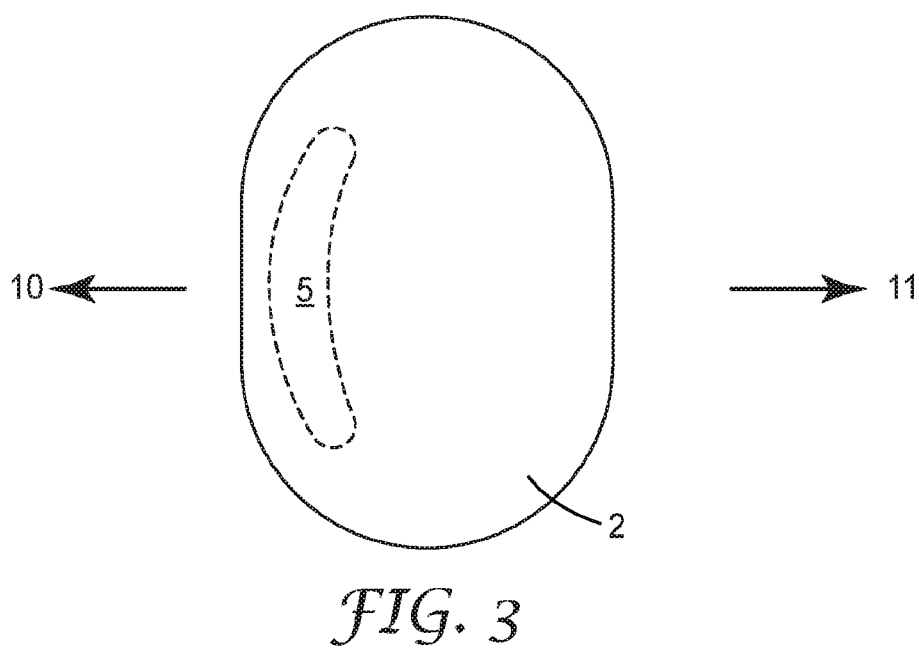
FIG. 3 is a top view on an earmuff for a hearing protector according to some embodiments of the present disclosure.

FIG. 3 in contrast shows a top view onto an earmuff 2 in accordance to the present disclosure. In the example the earmuff 2 has an acoustic membrane 5 which is arranged non-symmetrically. This means the attenuation provided by the earmuff 2 to sound originating from the anterior direction 10 is less than the attenuation provided by the earmuff 2 to sound originating from the posterior direction 11. Hence the earmuff 2 provides for a direction dependent attenuation.

Figure 4:
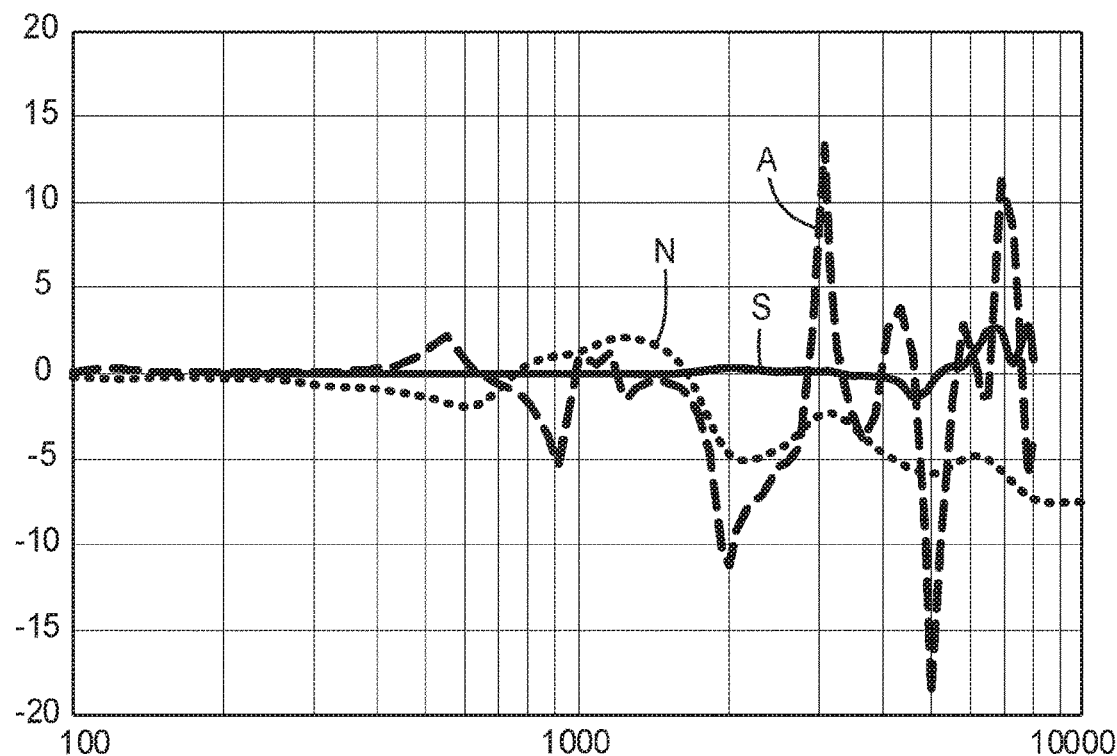
FIGS. 4, 5 are diagrams illustrating direction dependent sound level differences for a sound profile over a frequency range resulting from a simulation of the principle of the present disclosure.
Figure 5:
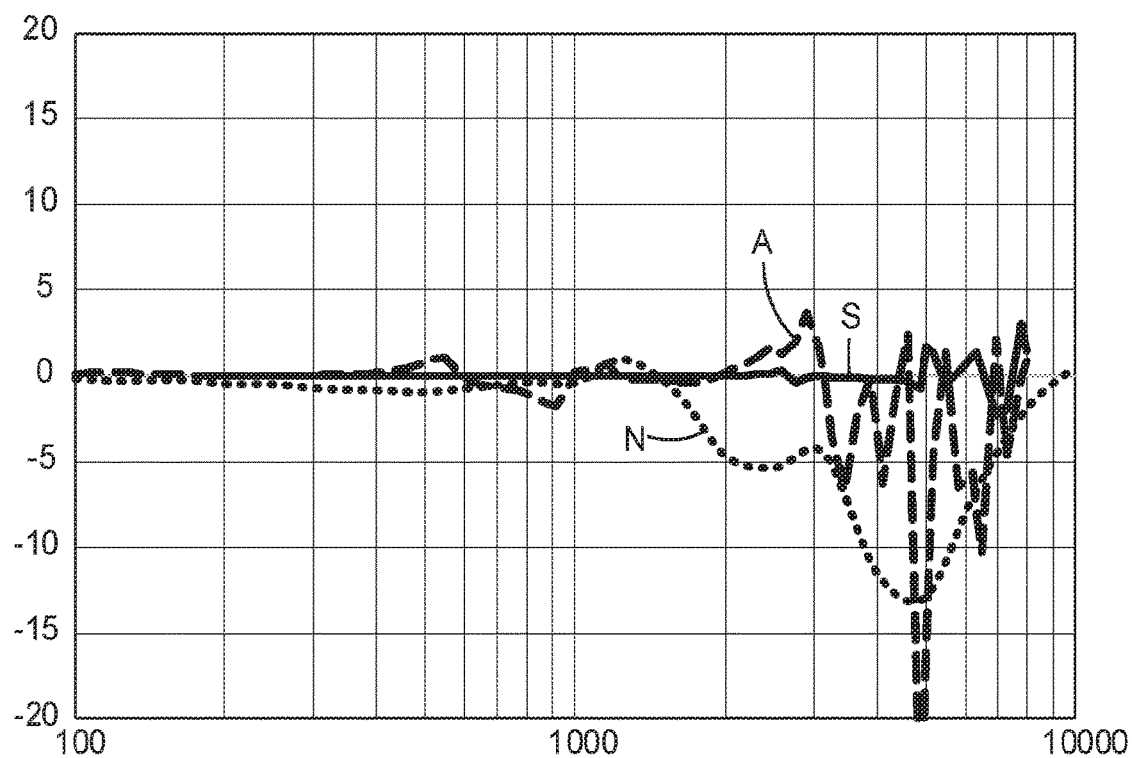

FIGS. 4 and 5 are diagrams illustrating a simulation of sound arriving from different directions in a person's ear. The sound simulation was performed by computer aid based on the earmuff designs shown in FIGS. 2 and 3. Each of the diagrams exhibits three curves N, S, A that each represent a level difference for sounds within a frequency range arriving in the ear from opposite directions. For example a sound originating from the anterior direction may have a certain level when arriving in the ear. When the same sound originates from the opposite direction that sound may have a different (for example lower) level. The difference between these levels is represented by the curves N, S, A of the examples for the frequency range specified in the diagrams. Curve N is based on sounds that arrive in the ear of a person that wears no hearing protector. Curve S is based on sounds that arrive in the ear of a person that wears a hearing protector that has a symmetrically arranged membrane in accordance to FIG. 2. And curve A is based on sounds that arrive in the ear of a person that wears a hearing protector of the present disclosure (shown in FIG. 3).

The diagrams illustrate in the vertical dimension the level difference in dB (Decibel) between sounds originating from opposite directions dependent on the sound frequency. In the horizontal dimension the diagrams illustrate the frequency of the sounds. Toward the left the diagram represents lower frequencies and toward the right higher frequencies of the sound. In particular, the diagrams illustrate a range of sound frequencies from 100 Hz on the left to 10000 Hz (or 10 kHz) on the right. The diagram for the representation of frequencies has a logarithmic scale.

For example at a sound frequency of 100 Hz there is no significant level difference between the directions from which the sound is originating. This would mean that at low sound frequencies, for example 100 Hz, a person could not perceive (even by turning the head) from which direction the sound originates because the sound level is substantially independent from the direction from which it originates. This is apparent from all three curves N, S, A which are substantially at about zero Decibel level difference in the frequency area of about 100 Hz to about 300 Hz. Toward higher frequencies the three curves exhibit significant different progressions. This means that for a sound having a higher frequency the person could perceive a difference depending on the direction from which the sound originates due to the level difference.

Curve N, which represents a sound profile arriving in a person's ear without hearing protection, provides basically a default or an ideal characteristic. In the diagram shown in FIG. 4 the level difference is illustrated for a sound profile originating from the anterior direction versus the same sound profile originating from the opposite (posterior) direction. The diagram shown in FIG. 5 illustrates the level difference for the same sound profile originating from a direction 45 degrees from the anterior direction and an opposite direction thereof.

As apparent from curve N of FIG. 4 in a frequency range of the sound profile of 2 kHz 10 kHz there is a clear and significant difference in the level arriving in the person's ear dependent on whether the sound originates from the anterior direction or the posterior direction. In this area the curve of curve N progresses entirely below the zero level. Due to this level difference the person's brain is provided with information that is useful for determining the direction from which the sound is originating. Looking at curve S, it can be seen that the same person wearing a hearing protector that is not in accordance with the present disclosure is taken away a significant part of such information. In particular in a frequency range of 100 Hz to 4 kHz there is basically no level difference. In the frequency range of 5 kHz to 10 kHz the level difference is much smaller than the level difference of curve N. Further, in the range of 5 kHz to 10 kHz a section of the curve progresses even in an area above zero level. The person who naturally correlates the level difference with a particular direction from which the sound originates thus may even perceive the sound originating from the opposite direction. Hence, the person wearing a hearing protector that is not in accordance with the present disclosure is hindered in recognizing the direction from which the sound is originating over a wide frequency range of the sound. Further, the person may even get confused about the direction from which the sound is originating.

As apparent from curve A the hearing protector of the present disclosure provides a much more significant level difference to the person's ear. Although the curve A exhibits peaks of level differences in the area above zero level the overall curve A follows the curve N much better than the curve S. This is particularly apparent from FIG. 5 which represents a situation in which the angle of the direction from which the sound originates is offset by 45 degrees relative to the anterior direction. Therefore although there are peaks of level differences in the area above zero level these peaks are in a relatively narrow frequency range, and due to the overall progression below zero level a person can better determine the origination of the sound, for example by slightly turning the head.

Figure 6:
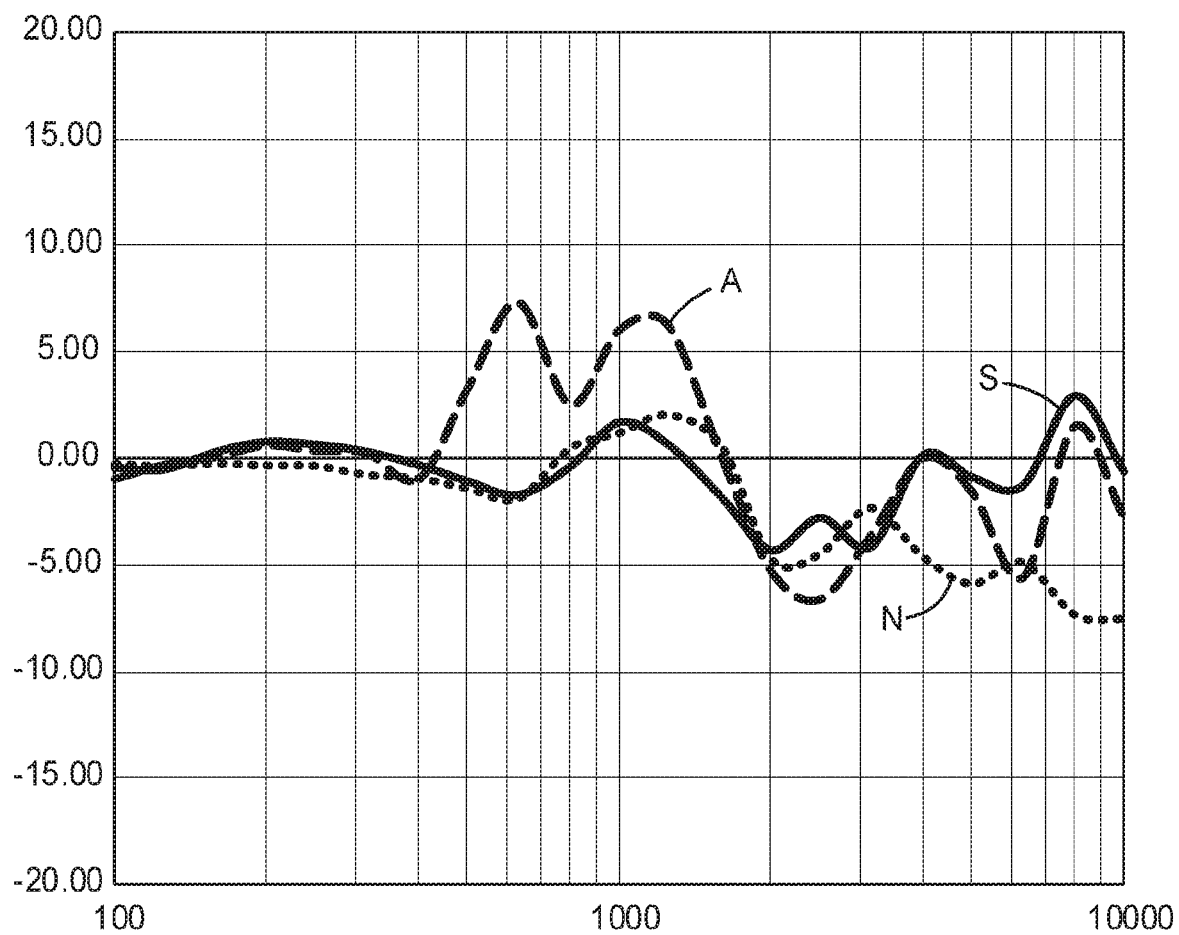
FIGS. 6-11 are diagrams illustrating direction dependent sound level differences for a sound profile over a frequency range resulting from test results of a hearing protector according to the present disclosure.
Figure 7:
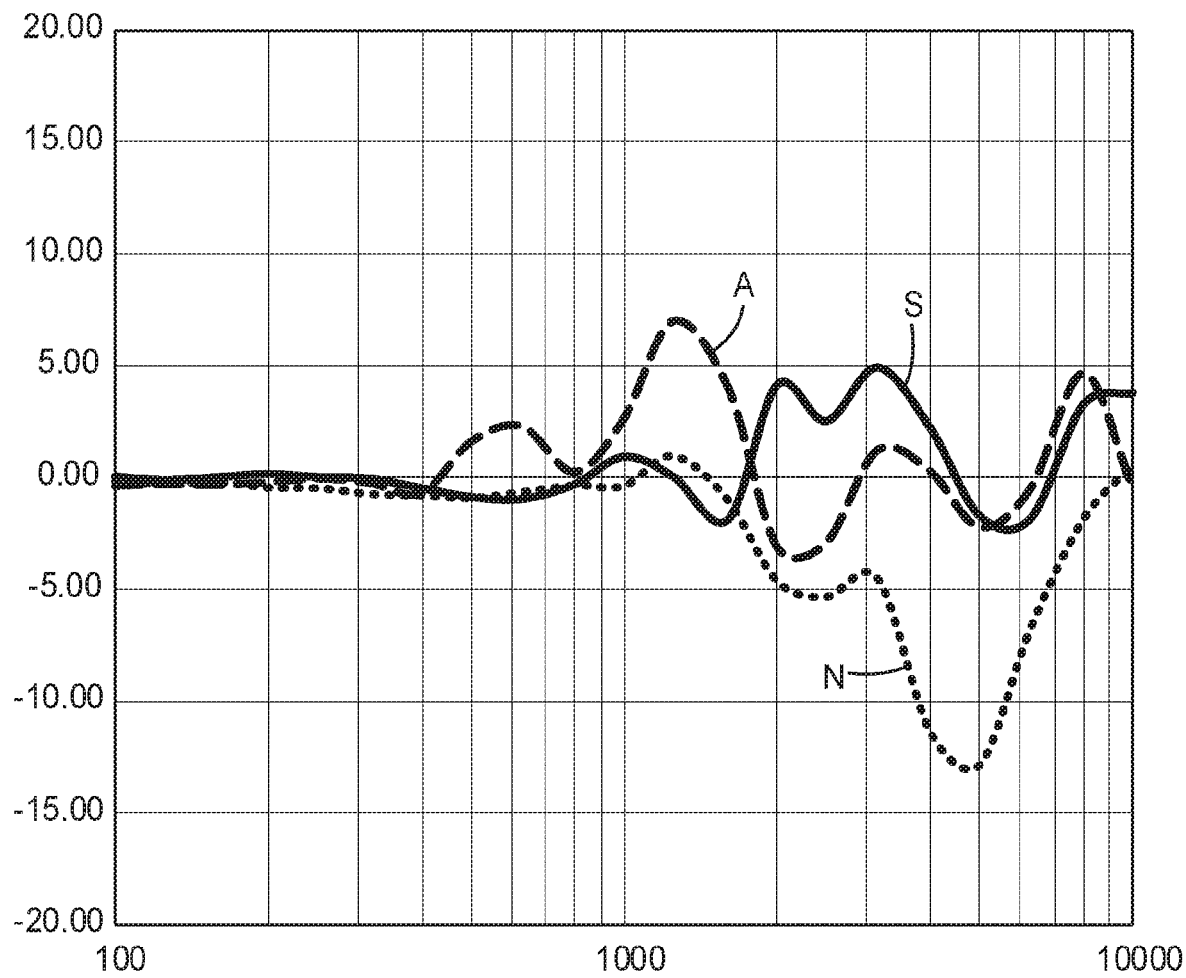

FIGS. 6 and 7 are based on measurements performed with a KEMAR. KEMAR is a head and torso simulator designed especially for acoustic research. It enables for example hearing aid and sound laboratories to perform simulated in-situ measurements of hearing aids and hearing protectors. KEMAR is available from GRAS Sound & Vibration A/S, Denmark. The diagrams of FIGS. 6 and 7 correspond to those in FIGS. 4 and 5 except that the curves N, S, A are based on measurements rather than a simulation.

Curve N was measured using the KEMAR without any hearing protection. The measurement was performed using one ear. The diagram in FIG. 6 represents a situation in which the KEMAR was oriented so that it directly faced the sound source and alternatively that it faced in the opposite direction. The diagram in FIG. 7 represents the situation in which the KEMAR was oriented angularly offset by 45 degrees with respect to the situation of FIG. 6. It can be seen that the measured curve N in FIGS. 6 and 7 essentially correspond to the simulated curve N of FIGS. 4 and 5.

Curves S and A were measured using the KEMAR in the same orientations as before and using the same sound profiles. However, curve S was measured with the KEMAR wearing a hearing protector of the type 3M™ Peltor™ Optime™ II, available from 3M Company, USA. Curve A was measured using the same type of hearing protector, but modified in accordance to the present disclosure. The measurements shown in FIGS. 6 and 7 are based on a 3M™ Peltor™ Optime™ II haring protector in which a membrane as illustrated in FIG. 1 was implemented in each earmuff. In this example the hearing protector was equipped with conventional cushions rather than cushions according to the present disclosure. Therefore a hole of 10 mm diameter was drilled through each earmuff on a side that faces the anterior direction when the hearing protector is worn. An adhesive tape having a thickness of 0.2 mm and made of PVC was used to close the hole so that that portion of the tape spanning the hole formed a membrane in accordance to the present disclosure. As apparent from FIG. 6 curve A approximates better to curve N in an area around 6 kHz than curve S. Further, in a frequency range of 2 kHz to 10 kHz curve A is offset relative to curve S in a direction toward the curve N. Looking at FIG. 7 it can be seen that in a frequency range of 2 kHz to 6 kHz the curve A progresses below the zero level difference. In the same frequency range the curve S extends over a significant section above the zero level. Therefore, in the frequency range of 2 kHz to 6 kHz the presence of the membrane according to the present disclosure enables a person to determine the origination of the sound better than with a conventional hearing protector.

Figure 8:
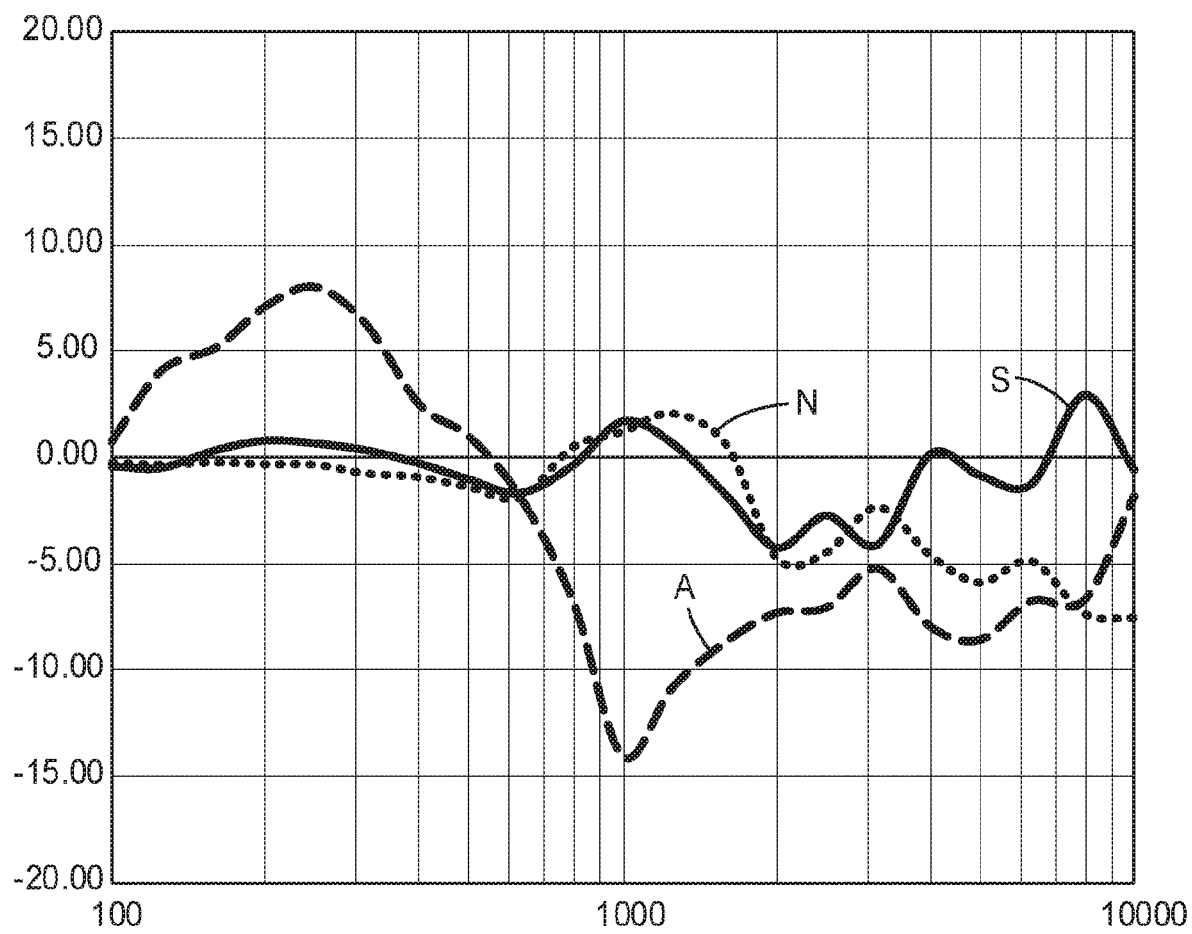
Figure 9:
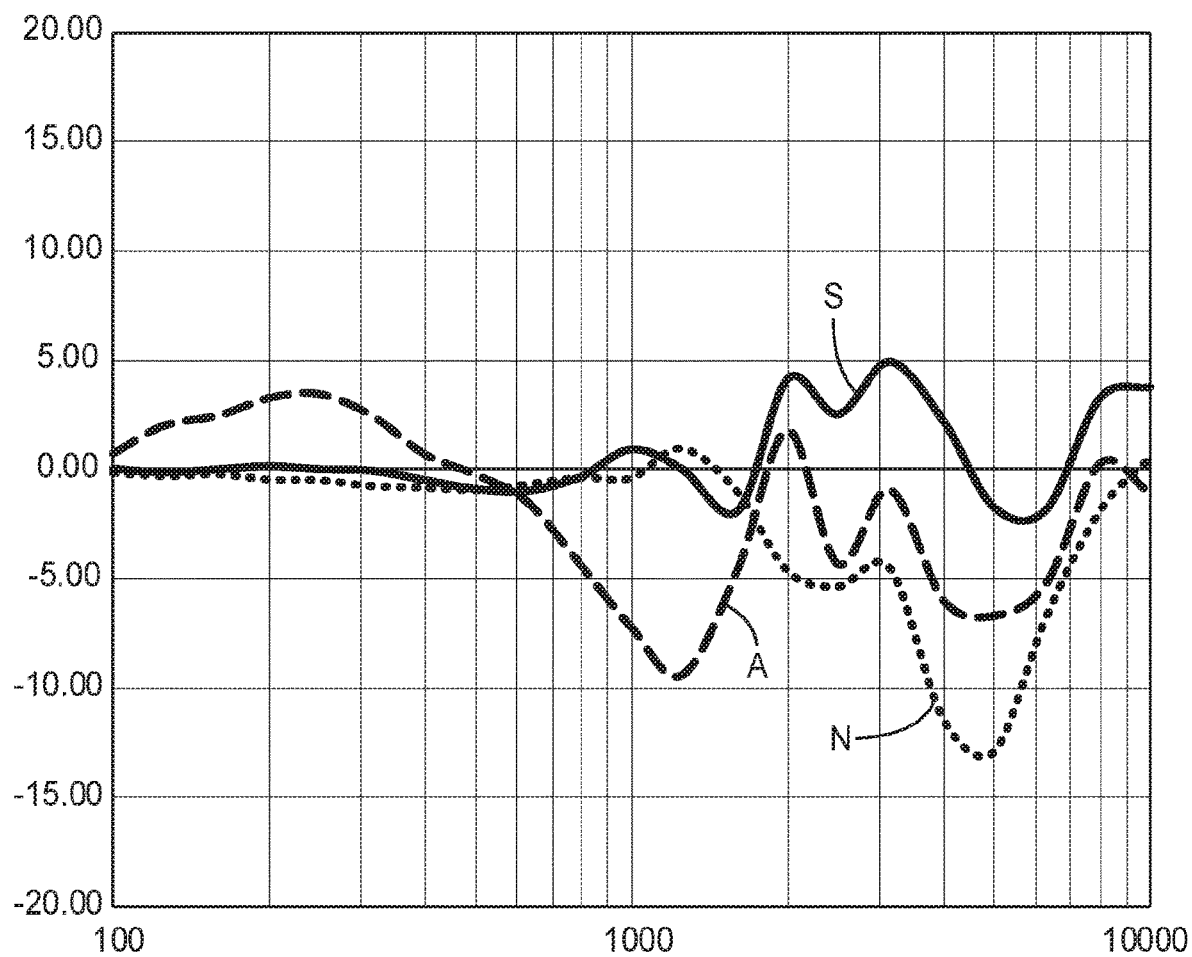

The same measurements as performed in the examples of FIGS. 6 and 7 were repeated with the conventional hearing protector 3M™ Peltor™ Optime™ II in which however the cushions were exchanged to cushions in accordance to the present disclosure (having holes 6 as shown in FIG. 1). The results are shown in FIGS. 8 and 9. As shown in FIG. 8 the level difference represented by curve A is very significant and even more significant than the level difference represents by curve N (without hearing protector). From FIG. 9 it is apparent that the curve A follows still closer the curve N than the curve S. Therefore, again the hearing protector according to the present disclosure enables better directional hearing than a conventional hearing protector.

Figure 10:
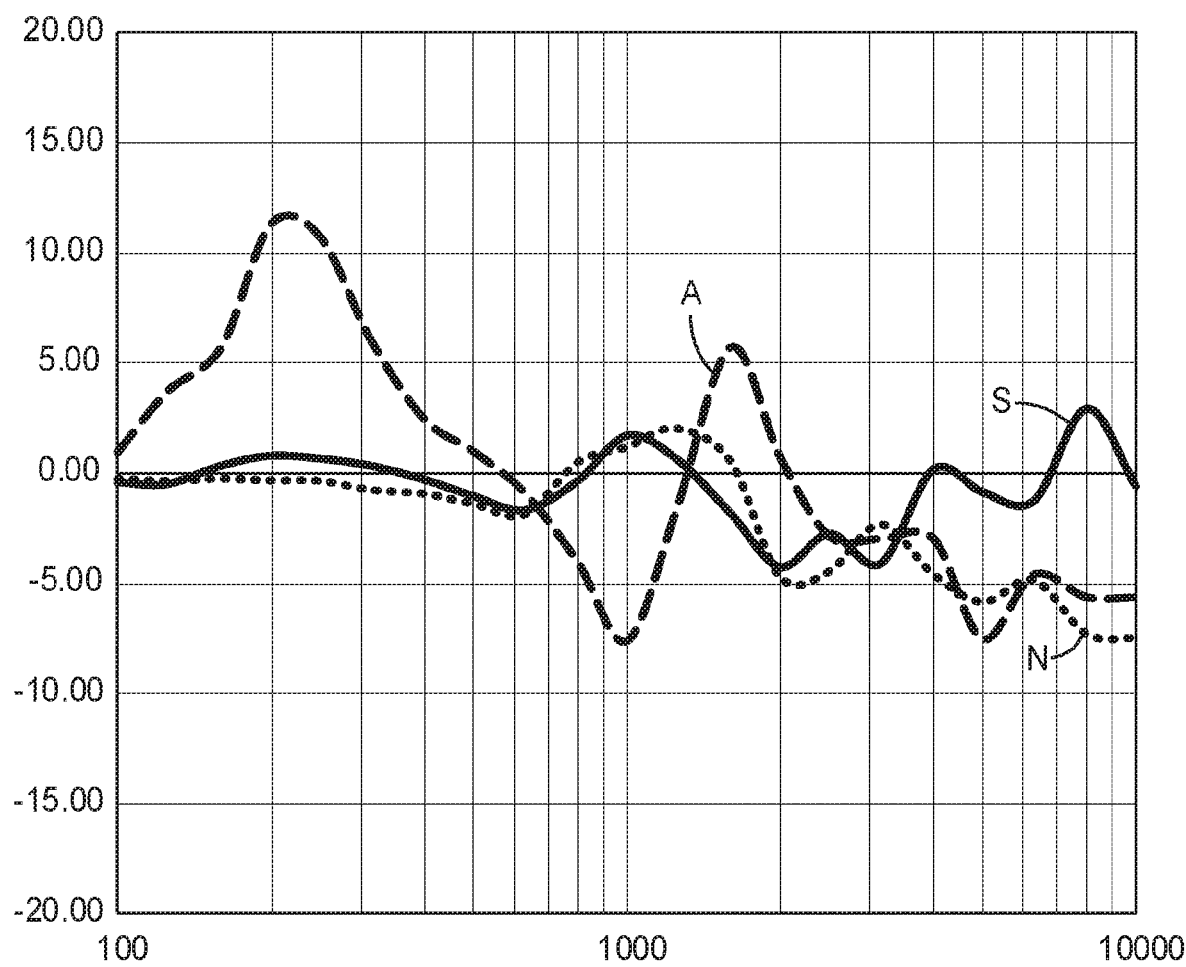
Figure 11:
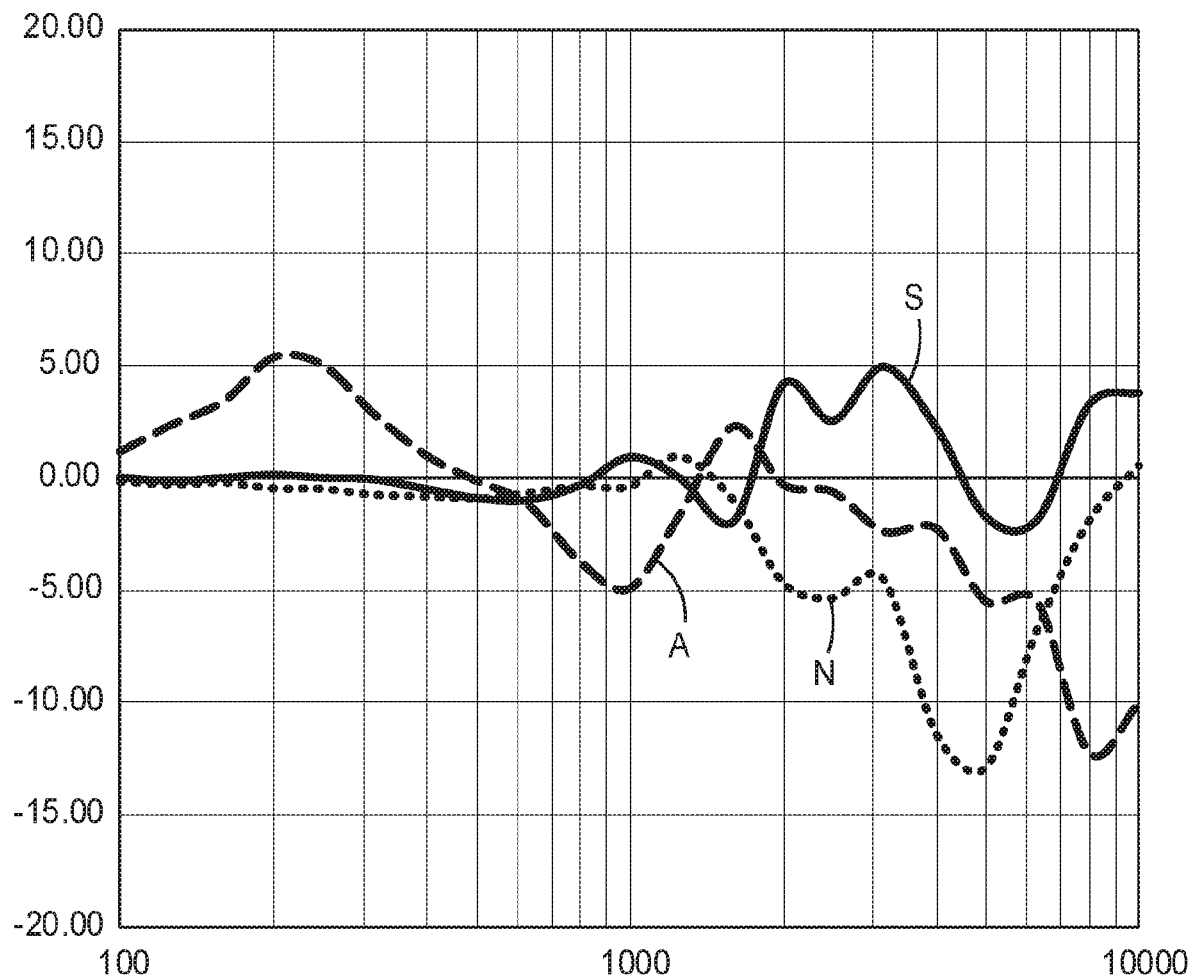

FIGS. 10 and 11 illustrate the results of measurements performed in the same way as described in the example of FIGS. 4 to 9 but using a hearing protector of the present disclosure in which the membrane in the earmuff and the holes in the cushion were combined. As shown, the curve A follows relatively well the curve N. Further, the curve A follows the curve N better than curve S. Therefore, the hearing protector of the present disclosure enables a better directional hearing than the conventional hearing protector.

It is noted that although the level differences between curves N and A are similar the absolute sound level was much lower when the hearing protector of the present disclosure was used as opposed to when no hearing protector was used.

The invention claimed is:

1. A hearing protector, comprising an earmuff, the earmuff comprising a cup-shaped shell providing a sound barrier, wherein the hearing protector comprises a sound inlet formed of at least one acoustic membrane that replaces a portion of the shell, and wherein the sound inlet locally reduces the sound barrier of the shell predominantly with respect to sound originating from an anterior direction, wherein the anterior direction is defined in accordance to on the anatomic directions of a wearer when the hearing protector is worn; and wherein the hearing protector comprises a second sound inlet formed of the at least one acoustic membrane that replaces a portion of the shell, and wherein the second sound inlet locally reduces the sound barrier of the shell predominantly with respect to sound originating from the anterior direction, and the membrane exhibits a resonance frequency that is within a range of 2 kHz to 6 kHz.

2. The hearing protector of claim 1, wherein the earmuff is formed of a front portion that faces in the anterior direction, and a rear portion facing in a posterior direction that is the direction opposite of the anterior direction, wherein the sound inlet is provided predominantly within the front portion.

3. The hearing protector of claim 1, wherein the shell is formed by a shell wall that has a smallest shell wall thickness and wherein the membrane is formed by a membrane wall that has a greatest membrane thickness, wherein the smallest shell wall thickness is greater than the greatest membrane thickness.

4. The hearing protector of claim 3, wherein the smallest shell wall thickness is within a range of 2 mm to 6 mm, preferably 4 mm.

5. The hearing protector of claim 3, wherein the greatest membrane thickness is within a range of 0.1 mm to 1 mm.

6. The hearing protector of claim 1, wherein the membrane extends in a first and a second dimension and wherein the smallest dimension in each of the first and second dimension is between 5 mm and 20 mm.

7. The hearing protector of claim 1, wherein the membrane has a circular, elongated or arced shape.

8. The hearing protector of claim 1, wherein the membrane is oriented in the anterior direction or at an angle of less than 90 degrees from the anterior direction.

9. The hearing protector of claim 1, wherein the membrane is made of a plastic material selected from among a thermoplastic polyurethane (TPU), acrylonitrile-butadiene-styrene terpolymer (ABS), polyvinylchloride (PVC), polypropylene (PP) and silicone.

10. The hearing protector of claim 1, comprising two or more membranes each replacing a portion of the shell, and wherein the membranes in combination form the sound inlet.

11. The hearing protector of claim 1, further comprising a cushion that is arranged at the earmuff for sealing with the wearer's head around the ear.

12. A hearing protector, comprising an earmuff, the earmuff comprising a cup-shaped shell providing a sound barrier and a cushion for sealing on a wearer's head, wherein the hearing protector comprises a first sound inlet formed of at least one hole in the cushion, and wherein the first sound inlet locally reduces the sound barrier of the cushion predominantly with respect to sound originating from an anterior direction, wherein the anterior direction is defined in accordance to on the anatomic directions of a wearer when the hearing protector is worn; and wherein the hearing protector comprises a second sound inlet formed of the at least one acoustic membrane that replaces a portion of the shell, and wherein the second sound inlet locally reduces the sound barrier of the shell predominantly with respect to sound originating from the anterior direction, and the membrane exhibits a resonance frequency that is within a range of 2 kHz to 6 kHz.

13. The hearing protector of claim 12, wherein the cushion is ring-shaped and forming a head facing side for contacting a wearer's head and an outer circumferential side extending between the earmuff and the head facing side, wherein the outer circumferential side is formed of a front portion and a rear portion being located toward the anterior direction and the posterior direction, respectively, when the hearing protector is worn by a wearer, and wherein the cushion comprises at least one hole through the front portion of the outer circumferential side.

14. The hearing protector of claim 12, wherein the earmuff comprises a loudspeaker.

\* \* \* \* \*